US012514516B2

(12) United States Patent
Gerder et al.

(10) Patent No.: US 12,514,516 B2
(45) Date of Patent: Jan. 6, 2026

(54) PROCESS AND CONTROL UNIT FOR COORDINATING ACOUSTIC SIGNALS OUTPUT BY DIFFERENT MEDICAL DEVICES

(71) Applicant: Drägerwerk AG & Co. KGaA, Lübeck (DE)

(72) Inventors: Henning Gerder, Lübeck (DE); Birger Landwehr, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 482 days.

(21) Appl. No.: 18/172,424

(22) Filed: Feb. 22, 2023

(65) Prior Publication Data

US 2023/0263483 A1 Aug. 24, 2023

(30) Foreign Application Priority Data

Feb. 23, 2022 (DE) ..................... 10 2022 104 256.1

(51) Int. Cl.
*G08B 21/04* (2006.01)
*A61B 5/00* (2006.01)

(52) U.S. Cl.
CPC ............ *A61B 5/746* (2013.01); *A61B 5/0002* (2013.01); *A61B 2560/0266* (2013.01)

(58) Field of Classification Search
CPC .................. A61B 5/746; A61B 5/0002; A61B 2560/0266
See application file for complete search history.

(56) References Cited

U.S. PATENT DOCUMENTS

| | | | | | |
|---|---|---|---|---|---|
| 3,949,388 | A | * | 4/1976 | Fuller | A61B 5/0008 128/903 |
| 4,308,872 | A | * | 1/1982 | Watson | A61B 5/417 600/534 |
| 4,625,733 | A | * | 12/1986 | Saynajakangas | A61B 5/0006 600/509 |
| 5,113,869 | A | * | 5/1992 | Nappholz | A61N 1/37258 128/903 |
| 5,490,505 | A | * | 2/1996 | Diab | A61B 5/7214 600/323 |

(Continued)

FOREIGN PATENT DOCUMENTS

| | | |
|---|---|---|
| CN | 103875034 A | 6/2014 |
| CN | 105027169 A | 11/2015 |

(Continued)

*Primary Examiner* — Quang Pham
(74) *Attorney, Agent, or Firm* — McGlew and Tuttle, P.C.

(57) ABSTRACT

A process coordinates the acoustic alarm signals output by different medical devices (1). A first medical device (1*a*) outputs, at a time interval before an output of a n acoustic alarm signal, a pre-signal which differs from the acoustic alarm signal with respect to at least one property. A further device receives the pre-signal output by the first medical device (1*a*) and carries out an analysis of the received pre-signal. As a function of a result of the analysis of the pre-signal, an alarm signal output unit (4) of a second medical device (1*b*) is driven in such a way that, as a function of the result of the analysis, at least one property of an alarm signal which is currently being output or will be output by the alarm signal output unit (4) is at least temporarily changed and/or a pre-signal is transmitted by the second medical device (1*b*).

20 Claims, 2 Drawing Sheets

(56) References Cited

U.S. PATENT DOCUMENTS

| | | | | | |
|---|---|---|---|---|---|
| 5,491,474 | A * | 2/1996 | Suni | G08C 17/00 | 340/870.31 |
| 5,630,413 | A * | 5/1997 | Thomas | A61B 5/6826 | 600/323 |
| 5,722,999 | A * | 3/1998 | Snell | A61N 1/37235 | 607/32 |
| 6,047,203 | A * | 4/2000 | Sackner | A61B 5/0006 | 600/509 |
| 6,100,806 | A * | 8/2000 | Gaukel | G08B 21/0211 | 340/8.1 |
| 6,366,805 | B1 * | 4/2002 | Lutz | A61B 5/383 | 600/544 |
| 6,988,215 | B2 * | 1/2006 | Splett | G06F 1/324 | 713/400 |
| 7,079,977 | B2 * | 7/2006 | Osorio | G16H 40/40 | 607/45 |
| 7,187,979 | B2 * | 3/2007 | Haubrich | A61N 1/37229 | 607/60 |
| 7,647,237 | B2 * | 1/2010 | Malave | G16H 40/67 | 700/214 |
| 7,937,137 | B2 * | 5/2011 | Cho | A61N 1/3622 | 600/515 |
| 8,175,076 | B2 * | 5/2012 | Pelzek | A61B 5/318 | 370/503 |
| 8,923,768 | B2 * | 12/2014 | Ma | H04B 1/74 | 455/509 |
| 9,183,720 | B2 * | 11/2015 | Miladin | G16H 10/20 | |
| 9,749,776 | B2 * | 8/2017 | Schönewerk | H04W 4/80 | |
| 10,758,176 | B1 * | 9/2020 | Feldman | A61B 5/746 | |
| 2001/0037222 | A1 * | 11/2001 | Platt | G06Q 10/10 | 705/3 |
| 2005/0206583 | A1 * | 9/2005 | Lemelson | A61B 3/113 | 345/7 |
| 2005/0235993 | A1 * | 10/2005 | Baecke | A61M 16/024 | 128/204.23 |
| 2005/0277911 | A1 * | 12/2005 | Stewart | G16H 40/67 | 700/282 |
| 2006/0242096 | A1 * | 10/2006 | Ozaki | A61B 90/06 | 706/23 |
| 2007/0179349 | A1 * | 8/2007 | Hoyme | G16H 50/70 | 600/300 |
| 2007/0251835 | A1 * | 11/2007 | Mehta | G16H 20/17 | 205/783 |
| 2007/0253021 | A1 * | 11/2007 | Mehta | H04L 61/5038 | 382/128 |
| 2007/0254593 | A1 * | 11/2007 | Jollota | G16H 40/67 | 455/67.11 |
| 2007/0255116 | A1 * | 11/2007 | Mehta | G16H 40/67 | 600/300 |
| 2007/0258395 | A1 * | 11/2007 | Jollota | H04W 72/23 | 455/67.11 |
| 2008/0027679 | A1 * | 1/2008 | Shklarski | A61B 5/681 | 702/182 |
| 2008/0208015 | A1 * | 8/2008 | Morris | A61B 5/165 | 600/301 |
| 2009/0081951 | A1 * | 3/2009 | Erdmann | A61B 5/002 | 455/41.2 |
| 2010/0168576 | A1 * | 7/2010 | Poland | G01S 7/5208 | 600/443 |
| 2010/0169513 | A1 * | 7/2010 | Levin | G16Z 99/00 | 710/18 |
| 2011/0054264 | A1 * | 3/2011 | Fischell | G16H 40/67 | 600/300 |
| 2011/0087756 | A1 * | 4/2011 | Biondi | G16H 40/67 | 709/217 |
| 2012/0083668 | A1 * | 4/2012 | Pradeep | A61B 5/6803 | 600/300 |
| 2013/0024206 | A1 * | 1/2013 | Hughes | G16Z 99/00 | 705/3 |
| 2013/0267792 | A1 * | 10/2013 | Petersen | G16H 40/63 | 600/301 |
| 2013/0310726 | A1 * | 11/2013 | Miller | G16H 20/40 | 717/173 |
| 2014/0074454 | A1 * | 3/2014 | Brown | G10L 15/08 | 704/235 |
| 2014/0304005 | A1 * | 10/2014 | Hughes | G06F 3/041 | 705/2 |
| 2015/0018723 | A1 * | 1/2015 | Lee | A61B 5/1118 | 600/595 |
| 2015/0213202 | A1 * | 7/2015 | Amarasingham | G16Z 99/00 | 705/2 |
| 2016/0012194 | A1 * | 1/2016 | Prakash | G06Q 30/0601 | 705/2 |
| 2017/0039822 | A1 | 2/2017 | Schlesinger et al. | | |
| 2017/0095217 | A1 * | 4/2017 | Hubert | A61B 5/742 | |
| 2018/0103859 | A1 * | 4/2018 | Provenzano | A61B 5/0024 | |
| 2018/0169314 | A1 * | 6/2018 | Gassman | A61M 5/14 | |
| 2018/0198594 | A1 * | 7/2018 | Tiirola | H04L 5/0051 | |
| 2018/0218123 | A1 * | 8/2018 | Gomez Sanchez | G16H 50/20 | |
| 2018/0286500 | A1 * | 10/2018 | Sole Guerra | G16H 15/00 | |
| 2018/0308451 | A1 * | 10/2018 | Saur | G06F 1/163 | |
| 2018/0325407 | A1 * | 11/2018 | Varadan | A61B 5/6831 | |
| 2019/0108314 | A1 * | 4/2019 | Moser | A61B 5/021 | |
| 2019/0286226 | A1 * | 9/2019 | Komaki | G06F 3/011 | |
| 2019/0298236 | A1 * | 10/2019 | Wynbrandt | A61B 5/7435 | |
| 2019/0392929 | A1 * | 12/2019 | Gassman | G16H 80/00 | |
| 2020/0021930 | A1 | 1/2020 | Iswanto et al. | | |
| 2020/0135334 | A1 * | 4/2020 | Rajasekhar | G10L 15/26 | |
| 2020/0388148 | A1 * | 12/2020 | Franz | A61B 5/1128 | |
| 2021/0022599 | A1 * | 1/2021 | Freeman | A61B 3/0025 | |
| 2021/0241889 | A1 * | 8/2021 | Johns | A61B 5/742 | |
| 2022/0331047 | A1 * | 10/2022 | Shelton, IV | G06F 3/011 | |
| 2023/0059282 | A1 * | 2/2023 | Pathak | A61B 5/1118 | |
| 2023/0070895 | A1 * | 3/2023 | Seguin | G16H 10/60 | |
| 2023/0395248 | A1 * | 12/2023 | Sipe | G16H 50/20 | |

FOREIGN PATENT DOCUMENTS

| | | | |
|---|---|---|---|
| CN | 106462658 | A | 2/2017 |
| CN | 107427229 | A | 12/2017 |
| CN | 109996489 | A | 7/2019 |

* cited by examiner

PROCESS AND CONTROL UNIT FOR COORDINATING ACOUSTIC SIGNALS OUTPUT BY DIFFERENT MEDICAL DEVICES

CROSS REFERENCE TO RELATED APPLICATIONS

This application claims the benefit of priority under 35 U.S.C. § 119 of German Application 10 2022 104 256.1, filed Feb. 23, 2022, the entire contents of which are incorporated herein by reference.

TECHNICAL FIELD

The invention relates to a process as well as to a control unit for coordinating acoustic signals output by different medical devices, wherein the output of an alarm signal by one medical device takes place in dependence on an alarm output by another medical device.

BACKGROUND

When monitoring patients in modern hospital wards and monitoring stations, especially in intensive care units, a large number of medical devices are used which, on the one hand, record patient condition values and, on the other hand, emit alarm signals when predefined threshold values are reached. Since such alarm signals are often output in acoustic form, it can happen that several alarm signals are heard at least partially simultaneously or at particularly short intervals in a patient room. This is particularly the case when several patients are treated in one room, as is often the case in intensive care units.

The noise level resulting from the condition described above leads to a sometimes considerable strain on treatment personnel, with the risk that individual alarms may no longer be perceived or may be perceived too late, thus endangering patient safety.

Based on the basic problem described above, the described danger can arise from the overlapping of several acoustic alarms of identical devices, acoustic alarms of devices of different types used on one patient, or acoustic alarms of different devices used on different patients.

For the future, further mechanization of the hospital environment can generally be assumed, and this will be accompanied by a further increase in noise emissions. The noise generated in hospital wards is caused both by technical building equipment, such as air conditioning systems, and by the medical equipment used to monitor and treat patients, both by the components required for their operation, such as fans, pumps or control units, and by the acoustic information and alarm signals output. Other sources of noise are conversations and movements of persons as well as treatment or care measures performed on the patient, such as repositioning.

The problem of noise pollution for treatment staff and patients is fundamentally well known. In this context, a pilot room was set up as part of a long-term trial at the Charité-Universitätsmedizin Berlin on the Virchowklinik campus to test alternative concepts in the design of intensive care units. In a project involving several companies, two rooms with four beds were redesigned in such a way as to provide maximum privacy for patients and their relatives. To this end, technical equipment was placed behind wall elements and alarm sounds were muffled or replaced or at least supplemented by targeted light signals. The noise reduction measures implemented led to an average reduction in noise levels of around 20 dB compared with conventional intensive care units. This has advantages for the quality of sleep and the length of stay of patients in an intensive care unit, but also with regard to the workload of the treatment staff.

Furthermore, the use of so-called noise traffic lights is known in this field, which are intended to draw attention to the exceeding of certain noise limits by means of an easily understandable display. Such noise lights, for example from the company SoundEar A/S, are often used in intensive care units, especially neonatal intensive care units.

In general, such are also known from other areas. For example, DE 20 2010 002 987 U1 describes a microcontroller-controlled noise traffic light that is primarily intended for noise minimization in school lessons.

Furthermore, the final report "Elbischger, A.: Lärmbelastung auf Erwachsenen-Intensivstationen. Klagenfurt 2009" (Noise Exposure in Adult Intensive Care Units) discusses the effects on the well-being of patients and nursing staff in intensive care units. In the context of the described project, among other things, measurements were carried out and the causes of noise were classified. It was confirmed that the main causes of noise are on the one hand person-related noise, for example caused by conversations in the room, footsteps or actions, and on the other hand equipment noise caused by operating noises, alarms and signal tones.

It is thus known that noise has a negative impact on the well-being or healing process of both healthy people and patients who are in an intensive care unit. To counter this problem, attempts have so far been made to alert users to the fact that a learning level has been exceeded, in particular by means of appropriate visual cues, or else to reduce the noise level of the signals output by individual medical devices. However, a corresponding reduction in noise level can only be carried out within certain limits to ensure that individual signals are not perceived or are perceived too late, which in turn would lead to an increase in patient risk.

SUMMARY

Based on the known technical solutions and the problems described above, the invention is based on the object of specifying a process and a control system by means of which noise pollution in hospital rooms, especially in intensive care units, can be reduced without increasing the risk to the patients being monitored. The system to be specified should also be applicable to an increasing number of medical devices that emit signals and alarms acoustically, and should be expandable in as simple a manner as possible. Furthermore, the technical solution to be specified should ensure that, while reducing the noise exposure for patients and treatment staff, a reliable differentiation of individual alarms takes place so that optimal monitoring and treatment of a patient is ensured at all times.

The task described above is solved with a process with process features according to the invention, with a control unit with control unit features according to the invention and a medical device with medical device features according to the invention. Advantageous embodiments of the invention are the subject of the dependent claims and are explained in more detail in the following description with partial reference to the figures.

The invention relates to a process for coordinating the acoustic alarm signals output by different medical devices, in which

- a first medical device outputs a pre-signal (preliminary signal) at a time interval before an output of an acoustic alarm signal, which pre-signal differs from the acoustic signal with respect to at least one property, at least a second medical device or another external control device suitable for signal evaluation receives the pre-signal output by the first medical device directly or after forwarding, and an analysis of the received pre-signal is carried out in an evaluation unit arranged in the second medical device and/or the external control device, and in which, as a function of a result of the analysis of the pre-signal, an alarm signal output unit of the second medical device is driven in such a way that, as a function of the result of the analysis, at least one characteristic of an alarm signal which is currently being output or will be output by the alarm signal output unit is at least temporarily changed and/or a pre-signal is transmitted by the second medical device.

An essential technical feature of the invention thus relates to the fact that, during the treatment and/or monitoring of a patient with the aid of at least two medical devices which are set up to emit acoustic alarm signals when an alarm threshold value for at least one patient condition value is reached, at least one of the medical devices is configured to emit a pre-signal even before the actual alarm signal is output, which pre-signal contains information about the future planned alarm signal emission. The output of an acoustic alarm signal is thus announced beforehand with the aid of a pre-signal. According to the invention, this pre-signal is received by the at least one second medical device and/or a suitable external control device and is analyzed by an evaluation unit to the effect that the currently occurring or future output of an acoustic alarm signal by the second medical device is influenced thereby. In addition or alternatively, it is conceivable that the second medical device also emits a pre-signal based on the analysis of the pre-signal, which in turn influences the future alarm signal output of the first medical device or the alarm output of a further medical device. The external control unit is an external unit that is preferably connected to a data technology infrastructure of a hospital for generating and transmitting alarms, to which the first and second medical devices are also connected either wirelessly or wired, The basic idea of the invention is thus to coordinate the acoustic alarm signals output by different medical devices during the monitoring of a patient, whereby a pre-signal is output by each of the medical devices, which is received and evaluated by the other medical devices or other devices. In this way, it is possible to prioritize different acoustic alarm signals occurring simultaneously or at least partially overlapping in a room with regard to their relevance for the patient's condition. Preferably, this involves suppressing individual alarms at least temporarily or adapting their volume and/or type to the relevance of the alarm signal.

The evaluation unit provided according to the invention, which carries out the analysis of the received pre-signal, is configured in such a way that the pre-signal as such and, on the basis of specific properties of the pre-signal, the type of alarm signal to be expected are recognized. In addition, it is also conceivable in principle that the evaluation unit is also configured in order to be able to achieve at least limited noise reduction when a medical device configured according to the invention is used together with a medical device not configured according to the invention. In this case, the evaluation unit is configured to detect an alarm signal from another medical device, to assign the other medical device to a class of medical devices on the basis of an analysis of the alarm signal, and to modify an alarm signal that is currently being output or will be output by the medical device according to the invention, taking into account the medical device class to which the other medical device belongs.

With regard to the type of pre-signal, generally this may be implemented as an electrical, optical or acoustic signal. Furthermore, the pre-signal may be transmitted wirelessly and/or by wire. Of course, combinations of the previously mentioned signal types and transmission paths may be used. In this context, it is advantageous if the pre-signal is configured and transmitted in such a way that it does not contribute to noise pollution in a room, or at least only to a very small extent.

In a particular embodiment of the invention, it is provided that the pre-signal is transmitted directly from the first to at least one second medical device, again the transmission may take place wirelessly or wired on the one hand and optically or acoustically on the other hand. In a particularly advantageous manner, the pre-signal is an acoustic signal with a frequency in the frequency range not audible by humans, i.e., before in the so-called ultrasonic range.

Alternatively or in addition, the pre-signal may be transmitted by wire, for example as an electrical signal, or as a light signal either wirelessly or wired at least partially via an optical waveguide. Further possibilities for transmitting the pre-signal envisage transmitting it via a wireless or wired network to which at least two medical devices, which are configured to emit acoustic alarm signals, are coupled.

Other special variants for the transmission of the pre-signal and the associated coordination of different medical devices issuing acoustic alarms, use an optical signal transmission with infrared signals, for example in a point-to-point signal transmission, a telemetric signal transmission, for example as a point-to-point signal transmission using Zigbee, Bluetooth, ISM, PMR and/or LPD (446, 868/902, 915). telemetric signal transmission, e.g. point-to-point signal transmission via Zigbee, Bluetooth, ISM, PMR and/or LPD (446, 868/902, 915), telemetric signal transmission in a network, e.g. via WLAN, Bluetooth, Mesh and/or NFC, acoustic signal transmission in the audible frequency range and/or wired electrical signal transmission in a network, e.g. via LAN, a power grid, Power-over-Ethernet, IOT and/or via industrial or building automation systems, such as Profibus.

In a particular embodiment of the invention, it is provided that a volume, a frequency, a modulation, a pitch, a tone type, a scale type (tone mode) and/or a melody of the alarm signal is changed depending on the result of the analysis. Thus, this embodiment provides that after analysis of a pre-signal has been performed, an output of an alarm signal currently and/or in the future by the medical device is adjusted in accordance with the analyzed characteristics of the pre-signal and, thus, the alarm signal announced by another medical device with the pre-signal. In this way, it is ensured that the output of an alarm signal is performed taking into account prioritization, wherein in particular a type and/or a volume of the alarm signal that is currently being output or is to be output in the future by the medical device analyzing a pre-signal is adapted to alarm signals already acoustically output and/or still to be output in the future by other medical devices. It is thus ensured that a volume or other characteristic of an alarm signal already output or to be output in the future is adapted to the importance of a threshold value exceeded causing the alarm or the risk existing for a monitored patient. Alternatively or in addition to a change or adaptation of the volume, a change in the modulation, frequency or melody of an alarm signal is also conceivable, so that two alarm signals output at least temporarily overlapping by medical devices can be clearly distinguished from one another by treatment personnel.

A further embodiment of the invention provides that, depending on the result of the analysis of a pre-signal, the alarm signal currently or in the future output by the alarm signal output unit of a medical device is at least temporarily interrupted. Also in this case, it is reliably ensured that the sound pressure level in a room is not unnecessarily increased even if at least two alarm signals are output at least temporarily simultaneously. The interruption of an alarm signal can in this case again be carried out taking into account the importance of an alarm, so that, for example, an alarm with a higher priority causes a continuous alarm signal, while an alarm with a comparatively lower priority is only output with interruptions.

It is of particular advantage if during the analysis of the pre-signal a prioritization of events underlying the output of an alarm signal, i.e. in particular violations of minimum or maximum threshold values for physiological parameters of a patient, is taken into account. Thus, during the analysis of the pre-signal, on the one hand, at least one property of the announced alarm signal or of the event on which the alarm planned for the future is based is determined and this event is compared with other events for which an output of alarm signals has occurred or has been announced. The individual events are prioritized in a suitable manner, so that an alarm signal has a higher priority whose underlying event has a higher importance for the patient's state of health. An alarm signal with a higher priority can thus, for example, be output with a higher volume, with a special sound signal, with a higher frequency and/or with a specific melody or tone sequence, while alarm signals with a lower priority are interrupted or output with a different volume, frequency and/or melody or in a different manner (visual display).

According to a special further development, it is provided that at least one patient-specific parameter and/or parameter specific to at least one of the medical devices is taken into account when determining the result on which the control of an alarm signal output unit is based. In this case, the analysis or, in addition to the analysis of the pre-signal, takes into account, for example, which patient is affected by an alarm-triggering event and what significance the corresponding alarm has for the respective patient. Device-specific parameters can also be taken into account, for example to indicate to the treatment staff that a medication, for example in a syringe pump, needs to be refilled or a device component needs to be serviced and/or cleaned.

In a further special embodiment of the process according to the invention, an environment of the first and/or the second medical device is monitored for the presence of persons, in particular treatment personnel, and a result of the environment monitoring is taken into account in the generation and output of a pre-signal and/or an alarm signal. With the aid of this technical embodiment, it is preferably determined before output of a pre-signal and/or alarm signal whether persons, in particular treatment personnel, are already present in the room and therefore at least one characteristic of an alarm signal to be announced or output is adapted accordingly, for example with regard to its volume, frequency, melody or tone sequence and/or its scale type. If, for example, it is determined that there is no one in the room other than the patient or patients, this is taken into account when determining the characteristics of an alarm signal and/or a pre-alarm and/or alarm signal is forwarded to a remotely located alarm output unit, such as a display on the ward corridor, a central monitoring unit, a pager, a tablet and/or a cell phone. In addition, in such a case, the output of an acoustic alarm signal in the treatment room can be dispensed with.

In a further embodiment of the invention, it is provided that a result of the analysis of the pre-signal is stored in a data memory for a stand-by period and is taken into account in the analysis of a further pre-signal and/or for the demand-responsive control of the alarm signal output unit. In this way, it is possible to store results of previously analyzed and/or output pre-signals in a data memory and to make them available for further processing so that they can be taken into account in the analysis of further pre-signals and/or in the generation of a control signal for driving the alarm signal output unit. Again, it is possible to prioritize the pre-signals, for which under certain circumstances no alarm signal has yet been output, in a suitable manner so that the relevance of different pre-signals or of events, in particular threshold value violations, on which the announced alarm is based can be taken into account. Again, the type and scope of the alarm, i.e. the characteristics of an announced or issued alarm signal, are adapted to the significance of the event for the patient.

According to a further embodiment of the invention, it is provided that during the analysis of the pre-signal, a result of an analysis of an alarm signal and/or a pre-signal of a further medical device is taken into account. According to this special further embodiment of the invention, it is thus possible to take into account the pre-signals and/or alarm signals output by a plurality of medical devices during the analysis and thus to adjust the characteristics of a pre-signal and/or alarm signal to be output in a particularly response-oriented (demand-oriented) manner. In this context, it is conceivable that not only the pre-signal of a further medical device is analyzed, but also alarm signals already output at this time are taken into account in the analysis. Also, a first medical device arranged in a room may transmit a pre-signal and at least a second medical device in the same room or at least in a reception area may analyze this pre-signal and, on the basis of the analysis performed, carry out a comparison of the priorities of the alarm signal already output with the announced alarm signal and thereupon preferably change at least one characteristic of the alarm signal already output by the first medical device on the basis of the analysis and the priority comparison.

Furthermore, a noise exposure characteristic value may be determined on the basis of alarm and/or pre-signals detected in a room, a suitable receiving and evaluation unit being provided for this purpose, which is arranged in one of the medical devices, in a central monitoring unit and/or in some other unit.

Preferably, the receiving and evaluation unit has at least one receiver, for example with a microphone or a piezoelectric transducer, for generating a measured value, at least one data memory, and a data processing unit. On the basis of the data processing carried out in the data processing unit, a signal is generated by the receiver and evaluation unit, a medical device, a central monitoring unit or another unit for controlling the medical devices arranged in a room or in a reception area, in particular the alarm signal output units, so that, after a suitable noise load (noise exposure) characteristic value has been determined, the output of alarm signals, in particular the sound pressure level (noise level) in a room or reception area, is adjusted so that a predetermined threshold value is not exceeded. According to a special further development, a corresponding noise load characteristic value is taken into account in the analysis of a pre-signal and/or the control of an alarm signal output unit of a medical device, so that overall a permissible sound pressure level is not exceeded by the acoustic alarm signals output by all the medical devices arranged in a room.

In addition to a process, the invention also relates to a control unit of a medical device or a central monitoring system that is arranged to perform a process according to at least one of the embodiments described above. Such a control unit is thus adapted to cause the output of a pre-signal, to control or perform the analysis of a pre-signal output from other medical devices, and to control an alarm signal output unit based on the result of the analysis of the pre-signal with respect to an acoustic alarm signal output adapted to the noise situation in the room. In this case, too, the control unit, when controlling the alarm signal output unit, may take into account not only the results of the analysis of the pre-signal, but also other measured values, for example from an environment monitoring system, and/or data, such as a specified noise load characteristic value.

Further, the invention relates to a medical device or central monitoring system having a control unit as previously described.

In general, a range of the pre-signals output by the individual medical devices may be limited to a specific area. In this way, it is also possible in larger medical care units, for example in large intensive care units or in emergency care tents, to create individual care islands, in particular by using groups of medical devices to treat and monitor patients. By forwarding suitable pre-signals and/or alarm signals to a central monitoring unit, it is in turn possible to inform treatment personnel of an alarm that has occurred in a particular island. Irritation caused by alarms issued in parallel can be prevented by adapting the various acoustic alarm signals in accordance with the invention, since treatment personnel are able to identify directly the alarm with the highest priority.

In the following, without limiting the general concepts of the invention, the invention is explained in more detail by means of embodiment examples with reference to the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
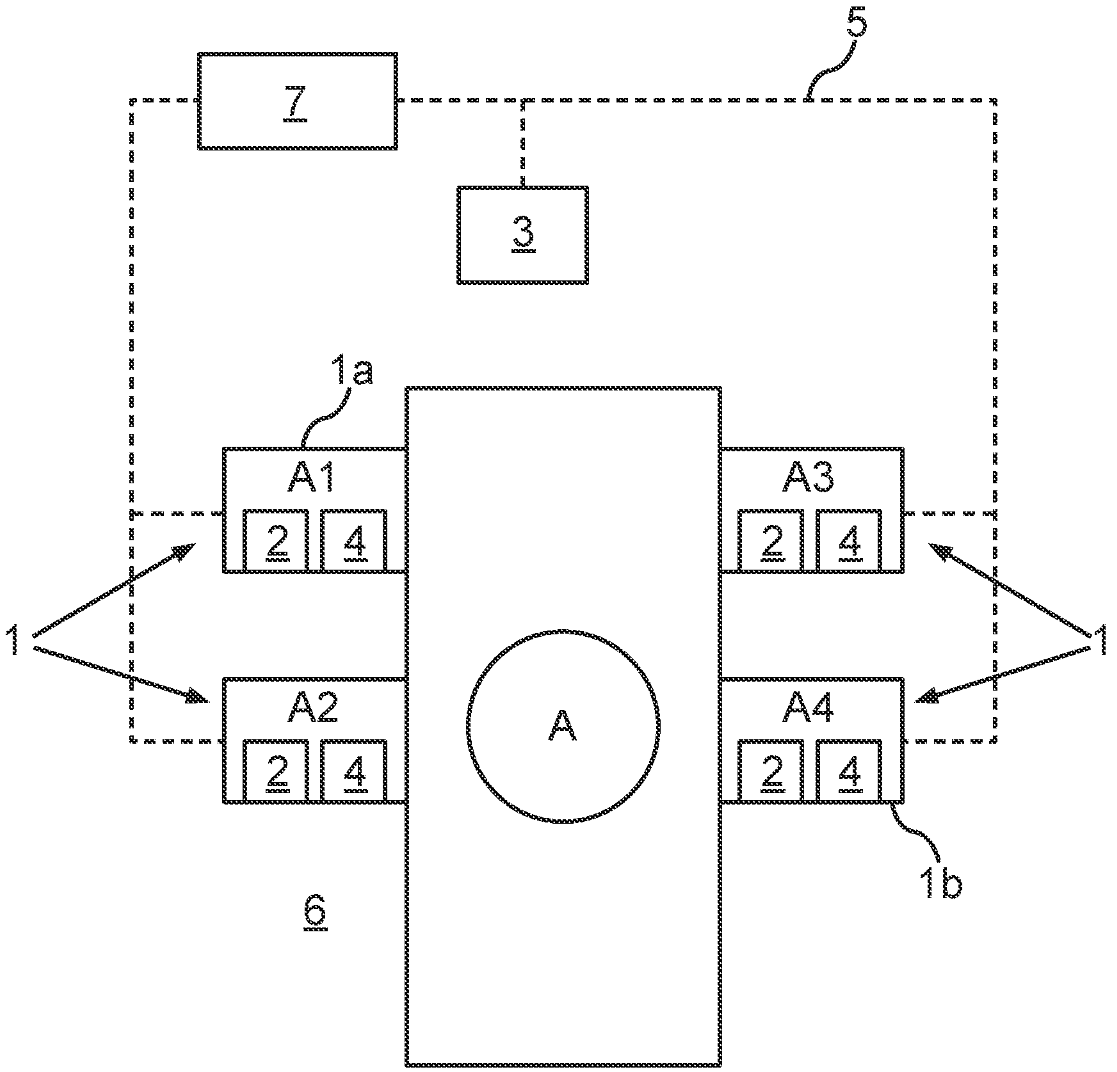
FIG. 1 is a schematic diagram of the arrangement of a plurality of medical devices at a bedside for the treatment and monitoring of a patient.

Referring to the drawings, FIG. 1 schematically shows the arrangement of a plurality of medical devices 1 for treating and monitoring a patient A, which are arranged in the area of the patient's bed. The number and type of medical devices 1 used can vary considerably, in particular due to the disease to be treated and the state of health of a patient. The medical devices 1 arranged in the area of the patient bed according to FIG. 1 are a ventilator A1, a patient monitor A2, a syringe pump A3 and an EIT device A4. The various medical devices 1 monitor a variety of physiological parameters of patient A, referred to as patient condition values. In the individual medical devices 1 and/or in a central monitoring unit 7, permissible minimum and maximum threshold values are defined for various physiological parameters of the patient A, the violation of which, i.e. exceeding or falling below, results in an acoustic alarm signal being output by the respective medical device 1 arranged at the bedside, in particular an alarm signal output unit 4. In accordance with the relevance of the individual limit violations triggering an acoustic alarm signal for the patient's state of health, suitable priorities are assigned to these, which are also stored in the medical devices 1 or the higher-level monitoring unit 7.

According to the invention, the medical devices 1 are configured in such a way that, before an acoustic alarm signal is output, the planned output of an acoustic alarm signal is announced by transmitting a pre-signal, in this case a non-audible ultrasonic signal. The pre-signal is configured with regard to its frequency, frequency sequence, frequency characteristic, amplitude and/or phase according to the characteristic of the alarm signal to be announced or the threshold value violation underlying the alarm. In addition, a corresponding pre-signal is transmitted via another transmission path, in particular via a network 5, such as a WLAN network, to which the other medical devices 1 are also connected.

At least one of the other medical devices 1 arranged in the area of the patient bed or in a room 6 in which the patient bed is located and also provided for acoustic alarming are configured to receive and analyze the transmitted pre-signal directly or indirectly. Irrespective of whether the analysis of the pre-signal takes place in an evaluation unit 2 arranged in the medical devices 1 or in an external control unit 3, on the basis of the result of the analysis of the pre-signal output by a first medical device 1*a*, an alarm signal output currently being executed, planned or already announced by at least a second medical device 1*b* is changed or adapted and/or a pre-signal is also output by the second medical device 1*b*. In this way, in particular, the volume, the tone sequence or the frequency of the acoustic alarm signals output via the alarm signal output units 4 of the various medical devices 1 is adapted to the prioritization, i.e. relevance, of the respective alarm for the patient's state of health. Likewise, acoustic alarm signals with lower importance of the underlying alarm or other device messages may be output not continuously but intermittently.

The pre-signal is coded in such a way that the relevant information is decoded in the evaluation unit of another medical device 1 or an external control unit 3. The information can take the form of an additional audio signal coding as an impressed or modulated audio signal, for example in the form of a burst or chirp. In any case, the pre-signal is configured in such a way that it does not interfere with the interpretation of the simultaneously output acoustic alarm signals by the treatment personnel.

According to the embodiment example described here, a pre-signal is an acoustic signal with a frequency in a range that is usually no longer audible by humans, in particular above 27 kHz. In order to be able to receive such a pre-signal, the medical devices 1 and the external control unit 3 have suitable ultrasonic transducers with a piezo element, which convert the acoustic signal into an electrical measurement signal. As already explained, other forms of pre-signals, such as light signals in the infrared frequency range, radio-telemetric signals or other wired or wirelessly transmitted signals can also be used.

As soon as corresponding pre-signals and thus patient-related data are at least partially transmitted via a network 5, additional security measures, in particular encryption via https, S/MIME or VPN, are advisable, especially to protect the data transmission from manipulation.

In the embodiment shown in FIG. 1, information about the device type, the alarm type, i.e. the event underlying the announced alarm, the priority, in particular whether it is an emergency alarm warning or an operational message, the type of alarm signal sequence and the repetition rate of the announced alarm signal are output with the pre-signal. The other medical devices 1 located at the bedside or in the same room 6 and, if applicable, the external control unit 3 receive either directly or indirectly the outputted pre-signal, analyze it and are finally able to initiate the following measures as required by appropriately triggering their alarm signal output unit 4:

Control and adaptation of the acoustic alarm signal preferably taking into account the priorities of different alarms, for example by means of a time delay (alarm delay), so that, as far as possible, an acoustic superimposition of its own alarm signal with the alarm signal announced by another medical device 1 is avoided, Evaluation of the situation, in particular analysis of the own alarm situation in comparison to the medical device 1 which has announced the output of an acoustic alarm signal and, if necessary, output of a pre-signal, for example if a medical device's own alarm has to be output which has a higher priority than the one announced by another medical device 1, Changing the volume of an output audible alarm signal if at least one other medical device 1 simultaneously emits an audible alarm signal, as well as Forwarding of the pre-signal and/or at least one piece of information contained therein to a further device, e.g. a control or output unit on the hospital corridor, and/or to a central monitoring unit, in order to ensure comprehensive information or the initiation of further measures (locked door scenario).

Figure 2:
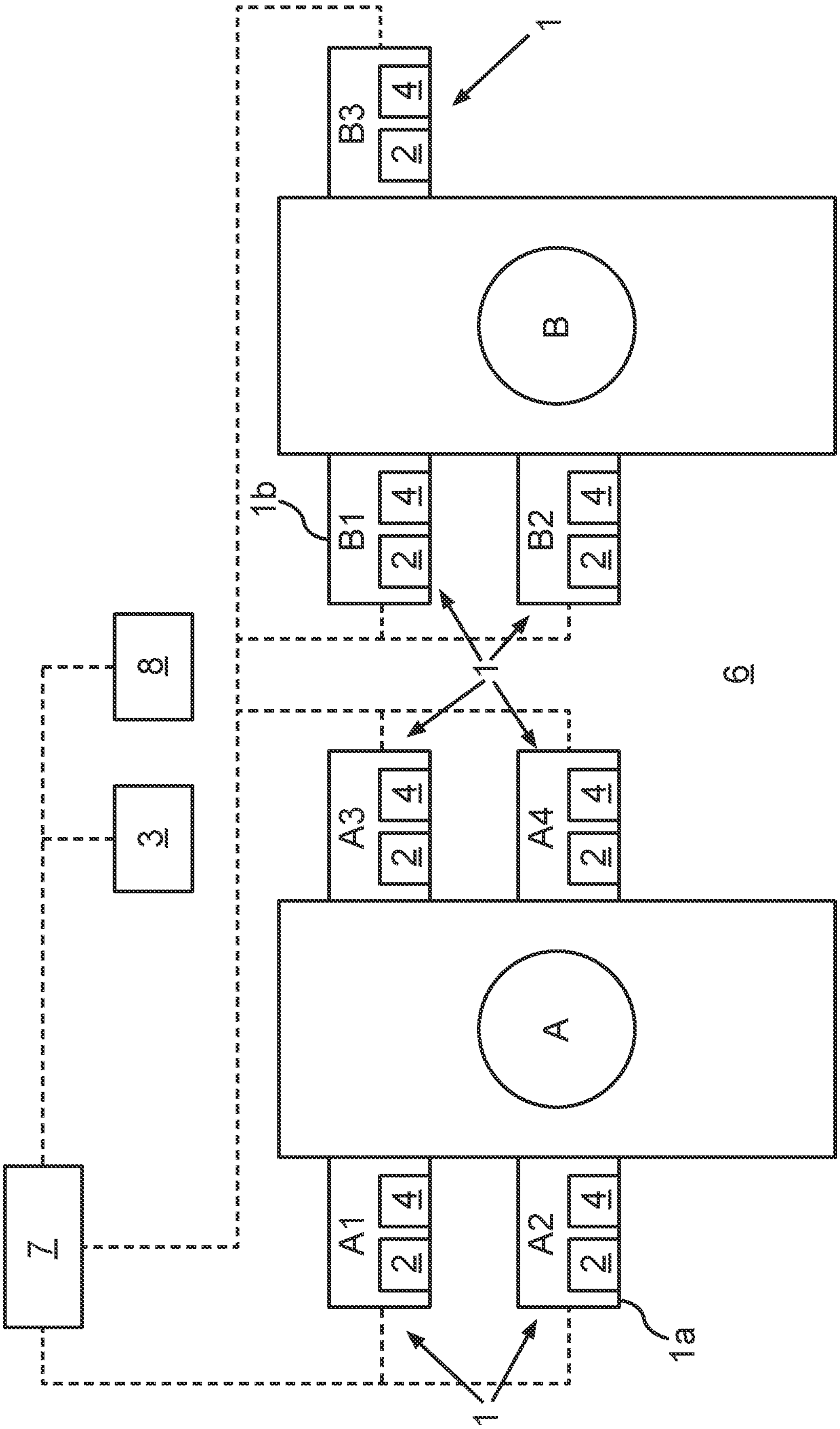
FIG. 2 is a schematic representation of two treatment stations arranged in one room, each allowing separate monitoring and treatment of a patient.

FIG. 2 shows a schematic diagram of a further exemplary embodiment of the invention, in which there are two patients in a room, of whom patient A is connected to four medical devices, namely A1, A2, A3 and A4, and patient B, to three medical devices, in this case B1, B2 and B3. Devices A1 and B1 are each ventilators, devices A2 and B2 are patient monitors, device A3 is a syringe pump, device A4 is an EIT device, and device B3 is a feeding tube. According to this embodiment, three-level alarm prioritization is provided, as shown in the following table:

| Device Name | Device Type | Alarm Type | Alarm Priority |
|---|---|---|---|
| A1 | Ventilator | MV low, MV high | I |
| | | VT low, VT high | II |
| | | f high | II |
| | | P high | I |
| | | FiO2 low | I |
| | | etCo2 high | I |
| A2 | Physiological Monitor (EKG, | Spo2 low | I |
| | HR, NIBP, SPO2, IBP, | BP low, BP high | II |
| | etCO2, Tcore) | HR low, HR high | I |
| | Arythmia | etCo2 high | II |
| | | tcore low, tcore high | III |
| A3 | Syringe Pump | Infusion amount used up | II |
| | | Occlusion | II |
| A4 | EIT Device | Inflection rate | III |

| Device Name | Device Type | Alarm Type | Alarm Priority |
|---|---|---|---|
| B1 | Ventilator | MV low, MV high | I |
| | | VT low, VT high | II |
| | | f high | II |
| | | P high | I |
| | | FiO2 low | I |
| | | etCo2 high | I |
| B2 | Physiological Monitor (EKG, | Spo2 low | I |
| | HR, NIBP, SPO2, IBP, | BP low, BP high | II |
| | etCO2, Tcore) | HR low, HR high | I |
| | Arythmia | etCo2 high | II |
| | | tcore low, tcore high | III |
| B3 | Peristaltic Pump/Feeding tube | Metered quantity reached | III |
| | | Occlusion | II |
| | | Empty supply | III |
| | | Disconnect | III |

Where:

MV: Minute volume

VT: Tidal volume f: Frequency

P: Print

FiO2: Inspiratory oxygen concentration etCO2: endtidal carbon dioxide content

SPO2: Oxygen saturation of the blood

BP: BP (Blood pressure)

HR: Pulse (heart rate)

NIBP: Non-Invasive Blood Pressure tcore: Core temperature

EIT: Electrical impedance tomography

In the embodiment shown in FIG. 2, the priorities for an alarm are set to the same for the same medical devices on both patients. Alternatively, it is conceivable that different prioritizations are provided depending on the patient's clinical picture and constitution. For example, the parameter HRhigh, i.e., the upper threshold value for the pulse, could be set with a different alarm priority for a patient with a stable constitution (stronger physical state). Alternatively, the upper threshold value HRhigh could be shifted further up.

Furthermore, the system described in connection with FIG. 2 for monitoring two patients A, B with a plurality of medical devices 1 arranged in one room has the option of issuing a so-called super alarm. As soon as an alarm signal is output for a longer period of time without being confirmed by a treatment person or without appropriate measures being taken, the priority of noise prevention is deliberately overridden and an alarm is issued by all medical devices 1. In this case, all medical devices 1 in the room 6, in particular the respective alarm signal output units 4, are controlled in such a way that a synchronized output of acoustic alarm signals takes place in order to very strongly increase the sound pressure level in the room 6. This results in an alarm amplification. In addition, information about the alarm is forwarded to at least one higher-level monitoring unit 7 and/or mobile output devices of the treatment personnel, such as pagers, tablets or cell phones.

It is further provided that all pre-alarm and alarm signals occurring in the room 6 are received by a special receiver module 8, prioritization is carried out and then the alarm with the highest priority is forwarded wirelessly or wired via a network 5 to an alarm output unit in a hospital corridor and/or at a central monitoring unit 7. Corresponding additional alarms are in turn issued acoustically and/or visually, for example via a display.

If, despite prioritization, at least two alarm signals have to be output simultaneously in the room 6 at least some of the time, the frequency position of the different alarm signals is adjusted, for example in the case of identical alarms output by different medical devices, to an audible difference of about 200 Hz. The adaptation again takes into account the analysis of the received pre-signals. It is essential in this case that, in particular, alarm signals output by different devices or types of devices in room 6 can be clearly distinguished from one another. Alternatively or in addition, a change or adaptation of the tone sequence, the change of single tones to chords or to five-tone sequences, as also provided for in the relevant standard, can be used to distinguish between device types.

While specific embodiments of the invention have been shown and described in detail to illustrate the application of the principles of the invention, it will be understood that the invention may be embodied otherwise without departing from such principles.

What is claimed is:

1. A process for coordinating acoustic alarm signals output by different medical devices, the process comprising the steps of:

with a first medical device, outputting, at a time interval before an output of an acoustic alarm signal, a pre-signal which contains information about the acoustic alarm signal and differs from the acoustic alarm signal with respect to at least one characteristic, wherein the first medical device outputs the acoustic alarm signal when an alarm threshold value for at least one patient condition is reached;

with a second medical device or an external control device, receiving the pre-signal output by the first medical device;

analyzing the received pre-signal in an evaluation unit of the second medical device or the external control device based on the information about the acoustic alarm signal; and controlling an alarm signal output unit of the second medical device as a function of a result of an analysis of the received pre-signal such that, as the function of the result, at least one characteristic of an alarm signal which is currently being output by the alarm signal output unit or will be output by the alarm signal output unit is at least temporarily changed and/or a pre-signal is output by the second medical device.

2. The process according to claim 1, wherein the pre-signal is configured as an acoustic, optical and/or electrical signal.

3. The process according to claim 1, wherein the pre-signal is transmitted via a wired and/or wireless network.

4. The process according to claim 1, wherein the pre-signal is transmitted directly from the first medical device to the second medical device.

5. The process according to claim 1, wherein a volume, a frequency, a modulation, a pitch, a tone type, an alarm type and/or a melody of the alarm signal is changed depending on the result of the analysis.

6. The process according to claim 1, wherein, depending on the result of the analysis, the alarm signal currently or in the future output by the alarm signal output unit is interrupted at least temporarily.

7. The process according to claim 1, wherein a prioritization of events underlying the output of an alarm signal is taken into account in the analysis of the received pre-signal.

8. The process according to claim 1, wherein at least one patient-specific parameter and/or parameter specific to at least one of the first medical device and the second medical device is taken into account when determining the result on which an activation of an alarm signal evaluation unit is based.

9. The process according to claim 1, wherein: an environment of the first and second medical devices is monitored for a presence of persons; and controlling the output of the pre-signal and/or alarm signal is at least partly based on a result of the environment monitoring.

10. The process according to claim 1, wherein a result of an analysis for a standby period is stored in a data memory and is taken into account in an analysis of a further pre-signal and/or for the control of the alarm signal output unit.

11. The process according to claim 1, wherein when determining the result of the analysis of the received pre-signal on which an actuation of an alarm signal output unit is based, a result of an analysis of an alarm signal and/or a pre-signal of a further medical device is taken into account.

12. The process according to claim 1, wherein at least one characteristic of the acoustic alarm signal from the first medical device is changed based on a pre-signal output from the second medical device.

13. The process according to claim 1, wherein a noise load characteristic value is determined on the basis of alarm and pre-signals detected in a room and is made available for further use in medical devices and/or a central unit for data storage, data processing and/or control of the medical devices.

14. The process according to claim 13, wherein the noise load characteristic value is taken into account in determining a result on which an activation of an alarm signal evaluation unit is based.

15. A control unit of a medical device or a central monitoring system for coordinating acoustic alarm signals output by different medical devices, the control unit comprising:

an input configured to receive a pre-signal output from a first medical device at a time interval before an output of an acoustic alarm signal from the first medical device, the pre-signal containing information about the acoustic alarm signal and differing from the acoustic alarm signal with respect to at least one characteristic; wherein the first medical device outputs the acoustic alarm signal when an alarm threshold value for at least one patient condition is reached; and an evaluation unit configured to:

analyze the received pre-signal based on the information about the acoustic alarm signal; and output a control signal to an alarm signal output unit of a second medical device to at least temporarily change an alarm signal which is currently being output by the alarm signal output unit or will be output by the alarm signal output unit as a function of a result of an analysis of the received pre-signal and/or to output a second medical device pre-signal by the second medical device.

16. The control unit according to claim 15, wherein a volume, a frequency, a modulation, a pitch, a tone type, an alarm type and/or a melody of the alarm signal is changed depending on the result of the analysis.

17. The control unit according to claim 15, wherein, depending on the result of the analysis, the alarm signal currently or in the future output by the alarm signal output unit is interrupted at least temporarily.

18. The control unit according to claim 15, wherein a prioritization of events underlying the output of an alarm signal is taken into account in the analysis of the received pre-signal.

19. The control unit according to claim 15, wherein:

an environment of the medical devices is monitored for a presence of persons; and outputting the control signal to control the output of a pre-signal and/or the alarm signal is at least partly based on a result of the environment monitoring.

20. A medical device or central monitoring system comprising:

an alarm signal output unit; and a control unit, the control unit comprising:

an input configured to receive a pre-signal output from another medical device at a time interval before an output of an acoustic alarm signal from the another medical device, the pre-signal containing information about the acoustic alarm signal and differing from the acoustic alarm signal with respect to at least one characteristic; wherein the another medical device outputs the acoustic alarm signal when an alarm threshold value for at least one patient condition is reached;

an evaluation unit configured to:

analyze the received pre-signal based on the information about the acoustic alarm signal; and output a control signal to the alarm signal output unit to at least temporarily change an alarm signal which is currently being output by the alarm signal output unit or will be output by the alarm signal output unit as a function of a result of an analysis of the received pre-signal and/or to output another medical device pre-signal from the medical device.

* * * * *